US006683695B1

(12) United States Patent
Simpson et al.

(10) Patent No.: US 6,683,695 B1
(45) Date of Patent: Jan. 27, 2004

(54) METHOD AND APPARATUS FOR DETECTING PROPERTIES OF REFLECTIVE TRANSPARENT SURFACE COATINGS ON A SHEET OF TRANSPARENT MATERIAL

(75) Inventors: Jeffrey A. Simpson, Peoria, IL (US); Mark A. Imbrock, Sylvania, OH (US)

(73) Assignee: Electronic Design To Market, Inc., Toledo, OH (US)

( * ) Notice: Subject to any disclaimer, the term of this patent is extended or adjusted under 35 U.S.C. 154(b) by 570 days.

(21) Appl. No.: 09/619,427

(22) Filed: Jul. 19, 2000

Related U.S. Application Data

(60) Provisional application No. 60/199,945, filed on Apr. 27, 2000, provisional application No. 60/188,075, filed on Mar. 9, 2000, provisional application No. 60/187,746, filed on Mar. 8, 2000, and provisional application No. 60/144,752, filed on Jul. 21, 1999.

(51) Int. Cl.[7] .............................................. G01B 11/06
(52) U.S. Cl. ...................................... 356/632; 356/445
(58) Field of Search ................................ 356/445, 447, 356/485, 504, 632, 239.7; 250/216, 559.28; 340/583

(56) References Cited

U.S. PATENT DOCUMENTS

| | | | |
|---|---|---|---|
| 1,503,543 A | 8/1924 | Lytle | |
| 1,756,785 A | 4/1930 | Gallasch | |
| 3,016,464 A | 1/1962 | Bailey | 250/219 |
| 3,137,756 A | 6/1964 | Gunther et al. | 88/14 |
| 3,693,025 A | 9/1972 | Brunton | 250/83.3 H |
| 3,807,870 A | 4/1974 | Kalman | 356/161 |
| 3,994,586 A | 11/1976 | Sharkins et al. | 356/73 |
| 4,207,467 A | 6/1980 | Doyle | 250/338 |
| 4,284,356 A * | 8/1981 | Heilman | 250/559.39 |
| 4,848,913 A | 7/1989 | Greiner | 356/382 |
| 4,899,055 A | 2/1990 | Adams | 250/372 |
| 4,902,902 A * | 2/1990 | Tole | 250/559.28 |
| 4,984,894 A | 1/1991 | Kondo | 356/382 |
| 5,054,927 A | 10/1991 | Garves | 356/382 |
| 5,237,392 A | 8/1993 | Hickel et al. | 356/381 |
| 5,239,488 A | 8/1993 | Markham et al. | 364/557 |
| 5,254,149 A | 10/1993 | Hashemi et al. | 65/29 |
| 5,442,573 A | 8/1995 | Bredberg et al. | 364/563 |
| 5,490,728 A | 2/1996 | Schietinger et al. | 374/7 |
| 5,525,138 A | 6/1996 | Hashemi et al. | 65/29.18 |
| 5,564,830 A | 10/1996 | Bobel et al. | 374/126 |
| 5,568,264 A | 10/1996 | Nakatsuka et al. | 356/394 |
| 5,581,355 A | 12/1996 | Myers et al. | 356/382 |
| 5,597,237 A | 1/1997 | Stein | 374/9 |
| 5,637,873 A | 6/1997 | Davis et al. | 250/339.11 |
| 5,657,124 A | 8/1997 | Zhang et al. | 356/355 |
| 5,726,749 A | 3/1998 | Schave | 356/239 |
| 5,726,756 A | 3/1998 | Aki et al. | 356/381 |
| 5,727,017 A | 3/1998 | Maurer et al. | 374/9 |
| 5,748,091 A | 5/1998 | Kim | 340/583 |
| 5,838,446 A | 11/1998 | Meth et al. | 356/372 |
| 5,966,214 A * | 10/1999 | Imbrock et al. | 356/632 |

FOREIGN PATENT DOCUMENTS

| | | |
|---|---|---|
| DE | 22584 | 1/1962 |
| EP | 0 480 027 | 4/1992 |
| GB | 2321309 | 7/1998 |
| JP | 53-16652 | 2/1978 |
| JP | 56-44804 | 4/1981 |
| JP | 60-147606 | 8/1985 |
| RU | 1585670 | 8/1990 |

* cited by examiner

Primary Examiner—Richard A. Rosenberger
Assistant Examiner—Vincent P. Barth
(74) Attorney, Agent, or Firm—MacMillan, Sobanski & Todd, LLC

(57) ABSTRACT

A method and apparatus for detecting properties of reflective transparent surface coatings on a sheet of transparent material, such as a sheet of glass or a sheet of plastic material. One or more light beams are directed at an angle to the surfaces of the material under test and the energy in surface reflections is sensed. The presence and surface location of a surface coating is determined from the relative magnitudes of surface reflections of the light beam. The type of coating is determined from the magnitudes of reflections from the surface coating of one or more different wavelength light beams. The surface coating may be, for example, a Low-E coating, or a metal or metal oxide coating left on a sheet of float glass.

23 Claims, 14 Drawing Sheets

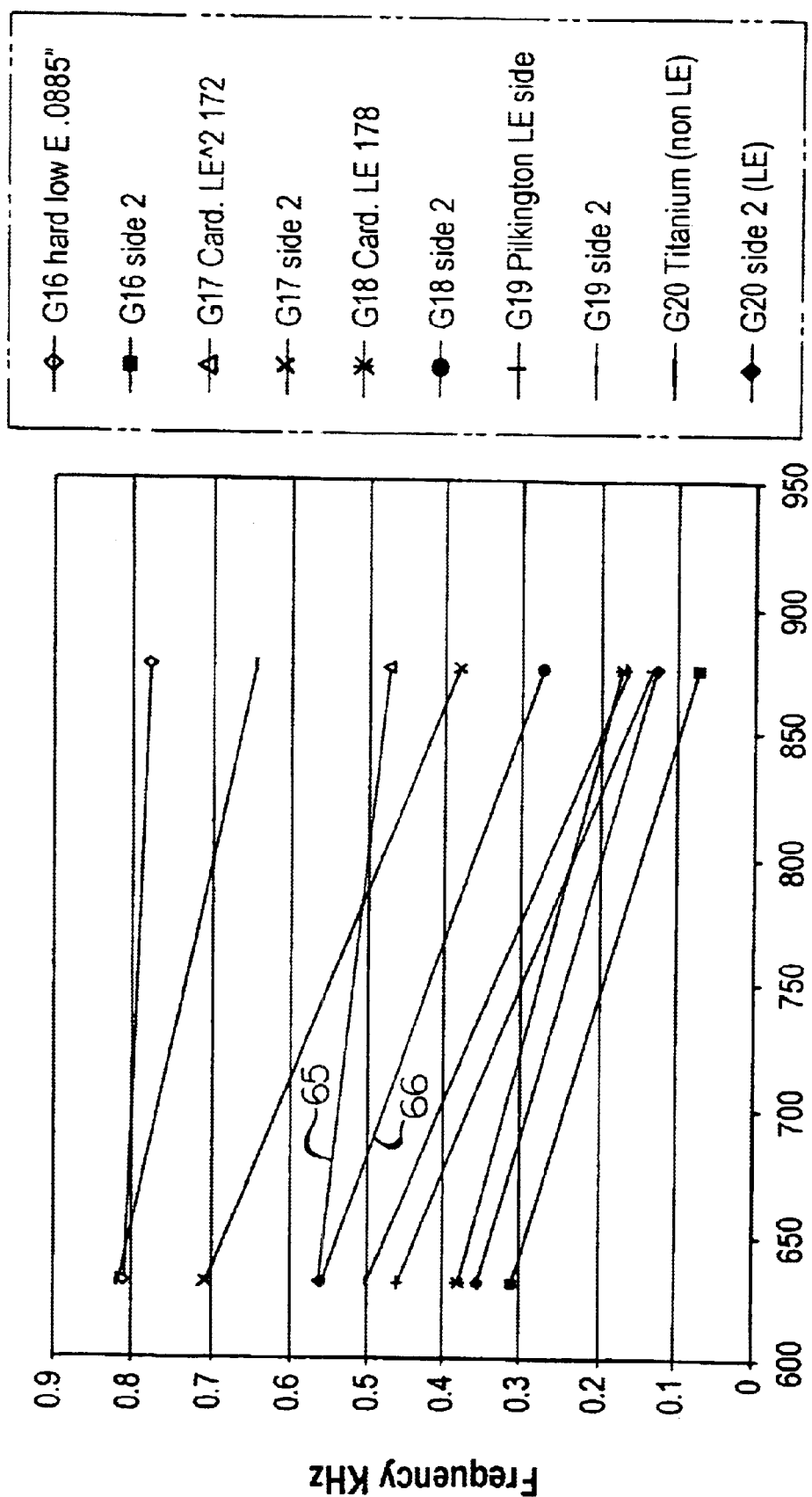

METHOD AND APPARATUS FOR DETECTING PROPERTIES OF REFLECTIVE TRANSPARENT SURFACE COATINGS ON A SHEET OF TRANSPARENT MATERIAL

CROSS-REFERENCE TO RELATED APPLICATIONS

Applicants claim priority to U.S. Provisional Patent Application Serial Nos. 60/144,752 filed Jul. 21, 1999, 60/187,746 filed Mar. 8, 2000, 60/188,075 filed Mar. 9, 2000, and 60/199,945 filed Apr. 27, 2000.

STATEMENT REGARDING FEDERALLY SPONSORED RESEARCH OR DEVELOPMENT

Not Applicable.

BACKGROUND OF THE INVENTION

The invention relates generally to detecting the presence, location and type of coating applied to various transparent mediums, or materials deposited directly to the surface or left on the transparent mediums during the manufacturing process (such as glass or plastic), that may be on a single sheet and/or multiple spaced sheets.

In the coating and glass industry, for example, there are numerous applications where residual coatings from the manufacturing process or spectral reflective coatings are applied to a transparent surface. For example, flat glass is commonly produced by a float process. The float process involves delivering a flow of molten glass at a controlled rate onto a relatively wide bath of molten metal, usually molten tin. The glass, which is buoyant on the molten metal bath, is advanced along the surface of the bath to form a uniform thickness layer which extends laterally across the surface of the bath. As the glass is continuously advanced along the bath, it is sufficiently cooled to permit it to be taken unharmed out of the bath by mechanical means. In the float process, traces of metal or of metallic oxides form on the bottom surface of the glass ribbon as it is removed from the molten metal bath. These oxides are substantially invisible to the naked eye and do not present any deleterious effects to the end use of the glass. However, it has been found that the bottom of the surface of the glass ribbon with the metal oxides has better planimetry than the top surface of the glass ribbon.

In the manufacture of laminated glass products, it is desirable to have the better planimetry on the outer surface. Also, in the process of coating glass with other materials, such as for Low-E windows, the surface containing the metallic oxides also needs to be known for the best performance. Consequently it is desirable to have a process and apparatus for continuously inspecting glass sheets for the surface containing the metallic oxides for identifying the better quality surface of the glass sheets.

U.S. Pat. No. 4,323,785 discloses one method for detecting the presence and locations of transparent metallic oxides on glass sheets. This process uses ultraviolet lamps to cause the metallic oxide to fluorescence and the resulting glow is detected with sensors. This process requires large lamps, which generally must be mounted within an extremely close distance of the material under test. Also, the process uses ultraviolet light which has human safety considerations.

In the coating industry, there also are numerous applications where spectral reflective coatings are applied to a transparent surface. Some of these applications include flat glass, windows, LCD screens, solar cell panels, thermal efficient films, as well as many other plastic and glass applications. During the processing of these flat materials, it is often desirable to have a apparatus that is able to detect the presence and location of the "invisible" coatings. The coatings may be located on one or both surfaces of a single piece of transparent material, or on one or more surfaces of multiple pieces of transparent material built into an assembly, separated by a known transparent media such as a gas.

It is desirable to have surface coating detection apparatus that can be implemented in a production process that will determine incorrect orientations of surfaces having transparent coatings prior to or during the production process. Many of these industries may not allow the medium to be contacted during the process to prevent contamination of or damage to the coating.

One method of detecting the presence and location of "invisible", electrically conductive coatings such as Low-E coatings is described in U.S. Pat. No. 5,132,631. A capacitor is formed between a probe placed against one surface of the glass and the coating. The value of the capacitor is determined by the presence or absence of an electrically conductive coating on the glass and by the location of any coating relative to the probe. This apparatus must contact the medium or be extremely near to the glass under test. The apparatus is limited in its effectiveness by the trade-off of capacitance change versus distance between multiple mediums in parallel. Thus the operator is required to know the glass thickness and air space of the window they are testing. Also the apparatus can not detect the presence of trace metallic oxides left over from the float glass process, determine the type of coating that is present nor detect any reflective characteristics of the coating.

U.S. Pat. No. 5,966,214 discloses a apparatus for measuring the thickness of a sheet of transparent material (such as a sheet of glass), and also for measuring the thickness and spacing of a composite formed from multiple-spaced sheets of glass. A laser beam is directed at an angle to the glass surfaces. The apparatus includes a gauge on which reflections of the laser beam impinge. The spacing between the reflections indicate the thickness of the sheets of glass and the sheet spacings. The apparatus is not designed for indicating the presence of reflective coatings on surfaces of the transparent material. The apparatus also requires that the laser beam be seen by the human eye, and is not designed for an automated production environment. Further, the apparatus was designed to be placed in contact with a surface of the transparent material.

Frequently it is necessary to identify if a transparent coating has been applied to a surface of a transparent medium that is considered a completed product. This completed product may be installed in a final field location. For example, some public utilities provide energy subsidies to homeowners that install specific types of energy efficient windows. It may be necessary to identify if a coating exists within the window assembly, as well as identify the type of coatings on the windows after they are installed in a house. This would allow the public utility to identify the type of coating to verify that the homeowner qualifies for potential energy subsidies.

Apparatus has recently been introduced which attempts to determine the category of a transparent surface coating for Low-E windows. The product classifies the windows as either low solar gain or high solar gain. A high solar gain window is often undesirable in homes located in warm climates. The apparatus consists of a single frequency (or wavelength) light beam that reflects off the coated surface under test. The amplitude of the reflection is measured and the apparatus attempts to determine if the coating is a low or high solar gain Low-E product, or if the glass is clear of a Low-E coating. The apparatus assumes that the surface under test has the same qualities as the surface of a sample used to calibrate the apparatus. Environmental concerns such as dirt on the media or environmental temperature can affect the amount of reflected light sensed by the apparatus. Also, at a fixed light frequency, two or more types of coatings may appear the same. A single point cannot accurately identify multiple coatings that reflect the same amount of relative light energy at a given point in the light frequency spectrum. Finally, this product can not identify the surface location of the spectral reflective coating.

BRIEF SUMMARY OF THE INVENTION

The invention is directed to a method and apparatus for detecting one or more of the presence, location and type of transparent surface coatings present on one or more surfaces of a transparent medium, such as a sheet of glass, or a sheet of plastic, or a composite formed from multiple spaced sheets of glass or plastic. The apparatus may or may not be in contact with the medium under test. The medium may be stationary or moving on a production line.

Depending upon the measurement being made, the apparatus may use one or more light sources. The light sources and sensing apparatus are in fixed positions relative to the medium being tested. A portion of a light beam is reflected from each surface of the material on to the light sensors. The sensors measure the reflections and supply this information to a programmed microcontroller, microprocessor or computer. The reflected signal from the medium under test provides the necessary information to determine the presence, location and/or type of coating. Depending on the desired information, the algorithm may use any combination of the following reflection data:

1. slope relationship of multiple frequency light sources;
2. the absolute value of the reflected signals due to different surfaces of the medium under test;
3. the ratio of reflected energy from each surface of the medium under test; and/or
4. the absolute power amounts of multiple surface reflections that have combined together on a linear type sensing array.

Generally the invention may be designed to operate in at least two configurations: production (factory) or field. The factory often requires apparatus that will not contact the medium under test to ensure that the integrity of the medium is not adversely affected. Field or work-site locations where the medium is being or has been installed in a final location, more often than not allows the medium to be contacted. At this point, the coating is usually sealed between multiple layers of the transparent medium.

Various objects and advantages of the invention will become apparent from the following detailed description of the invention and the accompanying drawings.

BRIEF DESCRIPTION OF THE DRAWINGS

FIG. 16 is a graph showing the curves for several commercial surface coatings, with each curve shown for each coating material on a first and second surface of a sheet of glass.

DETAILED DESCRIPTION OF THE INVENTION

Low-E glass has a spectral reflective coating applied to one surface to reduce energy loss through the glass. For float glass, traces of metal oxides naturally occur on the side of the glass which contacted the molten body of metal during the manufacturing process. Since these coatings and the glass are transparent, the glass and window manufacturers need apparatus to detect the side or sides of glass that contains the coatings. Often, this apparatus needs to operate without contacting the surface of the glass.

Figure 1:
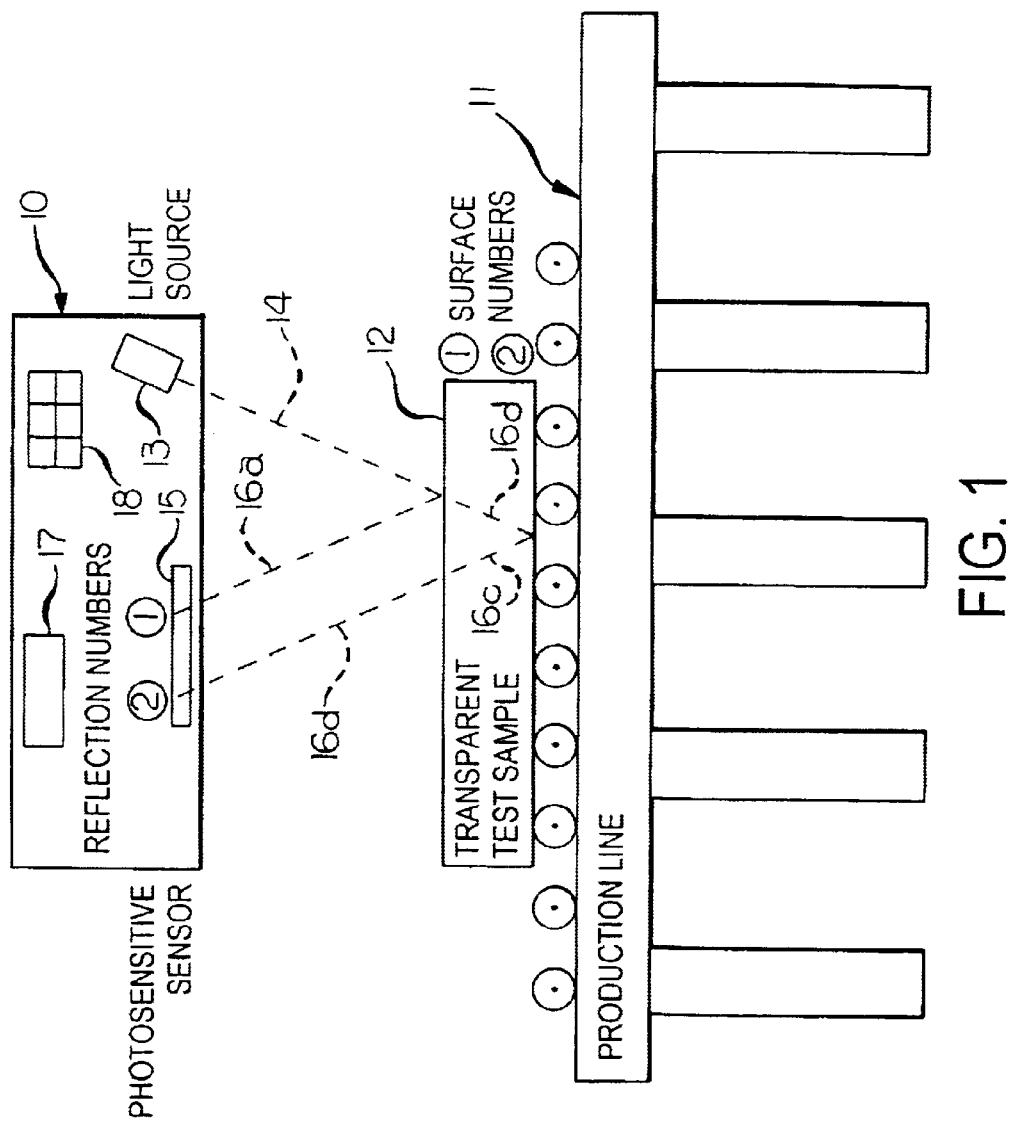
FIG. 1 is a diagrammatic view showing stationary apparatus according to one embodiment of the invention for detecting a reflective coating on a surface of a sheet of transparent material in a production environment.

FIG. 1 shows apparatus 10 mounted over a production line 11 on which a sheet of transparent material 12 is conveyed. The transparent material may be either a single sheet of material or a composite formed from two or more panes of transparent material. For the following description the material 12 will be described as sheets of glass. However, it will be appreciated that the transparent material 12 also may be a plastic or other transparent material. Bubble levels or other leveling devices (not shown) may be included on the apparatus 10 to guarantee parallel and perpendicular alignment to the production line 11 where the transparent material or glass 12 will pass. The apparatus 10 is preferably mounted over the top of the production line 11, for cleanliness, as well as for safety ramifications. However, it will be appreciated that the apparatus 10 also may be mounted below the production line 11.

The apparatus 10 has a concentrated light source 13 (laser or other) that projects a light beam 14. The light source 13 is aligned to direct the light beam at the glass 12 at a predetermined angle, for example, at about 30 degrees. A portion 16a of the beam 14 is reflected by a first or upper surface of the glass 12 back to a sensor 15, such as a linear CCD array, while another portion 16b of the beam 14 is refracted at the first surface as it passes into the glass 12. For the reflected beam 16a, the angle of incidence with the first surface of the glass 12 will equal the angle of the reflection back towards the sensor 15. The refracted portion 16b of the beam 14 will pass through the medium until it contacts the second (bottom) surface of the glass 12. Once again, a portion 16c of the beam portion 16b will be reflected by the second surface, and a portion (not shown) of the beam portion 16b will be refracted into the next medium. The reflected portion 16c of the beam portion 16b will pass through the medium 12 and impinge on the top surface of the glass 12. As before, a portion 16d of the beam portion 16c will be refracted back into the air. This refracted portion 16d will be directed toward the sensor 15 parallel to the original first reflection 16a (assuming that the top and bottom surfaces of the glass 12 are parallel).

For a single sheet of glass 12, this would conclude the description of the beam travel through the sample. If composite of multiple sheets of glass were being tested simultaneously (for example a double pane window glass assembly), the portion of the beam that passed through the first sheet of glass would continue into the second sheet of glass in the composite. The same reflection/refraction incidences would occur, allowing for evaluation of the second, third, . . . etc., surfaces. For the purposes of consistency in this application, the surface numbers increase with increased spacing from the light source 13.

It should be appreciated that the spacing between the light source 13 and the sensor array 15 will depend on the angle of the light beam 14 relative to the surfaces of the glass 12 and the spacing between the apparatus 10 and the glass 12. For example, if the angle of incidence between the light beam 14 and the first surface of the glass 12 increases from 30° to 45°, the spacing between the light source 13 and the points that the reflected beams impinge on the sensor 15 also will increase.

The reflections from the glass 12 are directed back toward the sensor 15 in the apparatus 10 mounted above the material 12. Filters (not shown) may be incorporated into the path of the reflected beams. The filters reduce the influence of ambient light by passing the reflected beams and blocking passage of much of the ambient lights. Inside the enclosure, the beam reflections 16a, 16d, etc. are projected onto the photosensitive sensor 15. Optionally, the beam reflections 16 may be filtered to remove various light frequencies before they impinge on the sensor 15. The sensor 15 includes an array of elements, which detect the location, and strength of each reflection 16a, 16d, etc.

The reflections from the glass surfaces may be detected by various commercially available sensors 15. For example, the sensor 15 may be one or more photosensors or a CCD array. The photosensors may be, for example, of a type which produce an analog signal having an output magnitude which is a function of the energy detected in the reflected light beam or of a type which produces a signal having a frequency which is a function of the detected energy in the reflected light beam.

The locations and strengths of the beam reflections 16a, 16d, etc. are fed into a programmed microcontroller, microprocessor or computer 17 in the apparatus 10 for evaluation. Although the following description refers to the microprocessor 17, it should be noted that the invention is not limited to any particular type of programmed device and that the programming may be by software, firmware or hard wiring. The microprocessor 17 mathematically evaluates the characteristics of each beam reflection 16a, 16d, etc. An algorithm that can incorporate location, peak values, intensity and weightings of each sensing element in the sensor 15 that is affected by the reflected beam determines the presence and location of the spectral reflective coating. As discussed below with respect to FIGS. 13–16, multiple concentrated light sources may be used to define the type of coating in addition to coating presence and location that was found from the peak information.

The electronics or program data for the microprocessor 17 may be factory calibrated, or may be trained in the field. For repeating applications, thresholds may be determined that can be set prior to shipping the apparatus 10 to the customer for a specified application. For varying conditions, the apparatus 10 may be delivered to the customer without any preset thresholds. Once installed in a production line setting, the apparatus 10 can be shown samples of the various types of glass that could occur during a typical production run and appropriate data is stored for each glass sample. Variations could include single and multiple panes of glass with no surface coatings and with coatings on different surfaces. The microprocessor 17 will store the variations in memory, and will be able to identify each type of glass as it is experienced in production by comparing the reflection data for the glass with the stored data.

Additional reflective sensors may be incorporated into the apparatus 10 to determine when a sheet of glass 12 to be tested is passing under the apparatus 10. Multiple sensors 19 may be provided to determine when the glass 12 enters the testing area, as well as when the glass 12 has exited the testing area.

Depending on the desired information, the microprocessor 17 may use any combination of the following reflection data:

slope relationship of multiple frequency light sources;

the absolute value of the reflected signals due to different surfaces of the medium under test;

the ratio of reflected energy from each surface of the medium under test; and/or the absolute power amounts of multiple surface reflections that have combined together on a linear type sensing array.

Once the apparatus 10 has evaluated the beam reflections, it can display the results via various indicators on a display panel 18. In addition, or alternately, output ports can be provided on the apparatus 10 to supply data for controlling #production. The data may include indicators:

coating on surface #1, the top surface, i.e. Low-E coating or traces of metallic oxide coating on surface #2, the bottom surface, i.e. Low-E coating or traces of metallic oxide no coating on either surface i.e. no Low-E.

coating on surface #3 of a composite coating on surface #4 of a composite

Where appropriate, there may be multiple data, as when coatings are present on more than one surface, or there may be additional indicators for multiple coatings. The outputs may be used, for example, to:

shut down the production line;

notify the operator of an incorrect orientation of the material 12;

notify quality control that a defective product is present; and/or provide downloadable data detailing any error conditions that occur, as well as the time and day of the occurrence.

Figure 2:
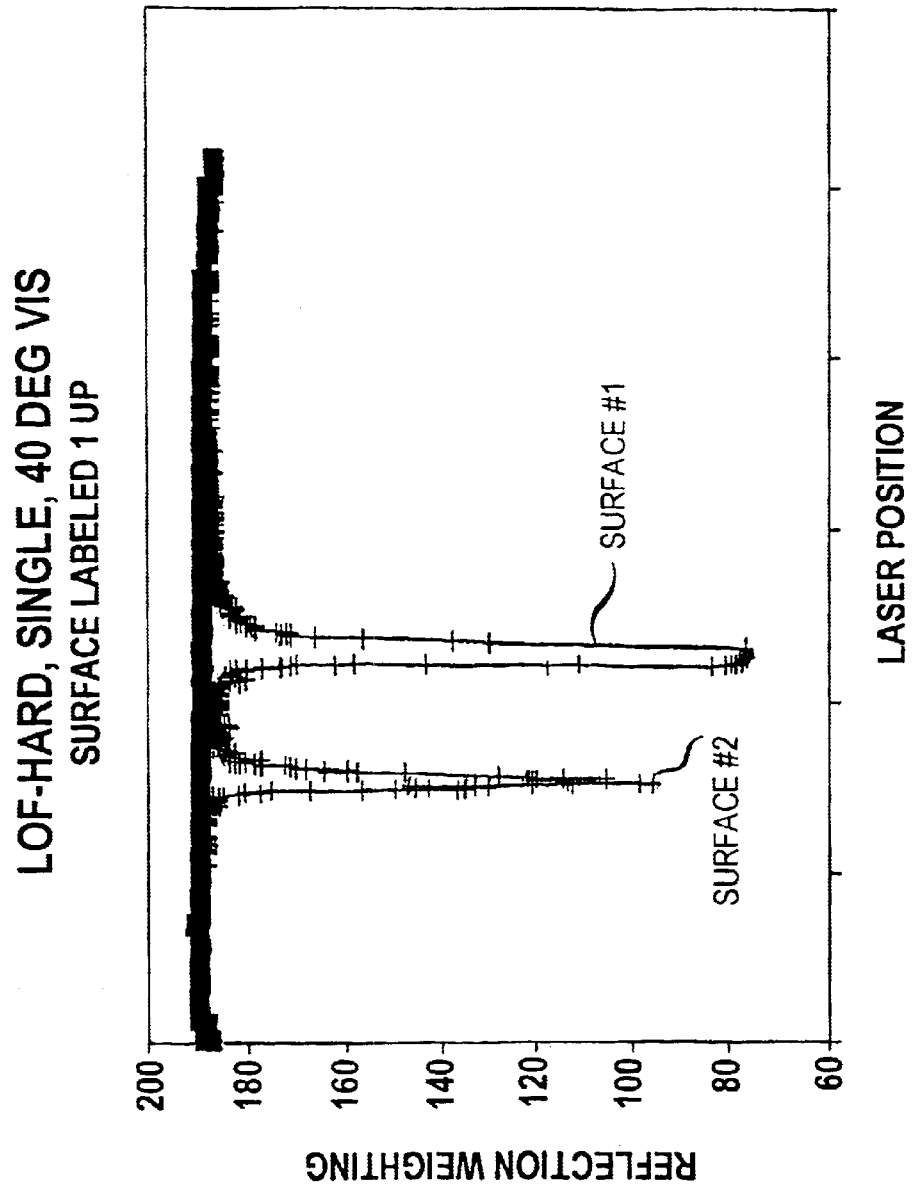
FIG. 2 is a graph showing exemplary reflections from a single sheet of glass having a transparent reflective coating on the first surface as detected by a linear sensing array.

FIG. 2 is a graph showing the sensor 15 measurement results found by the apparatus 10 for a single sheet of LOF glass having a Low-E coating on surface #1. The apparatus 10 can be programmed to determine the number of sheets of glass in a product based on the number of reflections or peaks found. The reflections may be taken with either a visible laser or an infrared laser. For this example, a visible laser was directed at a 40° angle to the first surface of the sheet of glass. For the illustrated single piece of glass, two surface reflections or peaks were detected by the sensor 15. Since the reflective coating is located on surface #1 of the glass, there is a larger area or weighting under the peak for surface #1 as well as a higher peak count. The algorithm of the microprocessor 17 generates the values shown in Table 1. These values allow for the determination of the presence and location of the coating.

The following Tables are created using a CCD array for the sensor 15. The selected commercially available CCD array has 2400 pixels, of which 1200 were used in taking the measurements. This provides a location resolution of about one thousandths of an inch (about 0.254 mm). In the following Tables 1–3, the lower or X axis represents the pixel location on the CCD array and the Y axis represents the weighting or magnitude of the reflection reading at each pixel location. The "Average Weighting" is the average value of the measurement at each pixel for a surface reflection, and the "Total Weighting" is the sum of the measurements at each pixel under each peak for a surface reflection or the area under the curve beginning at some arbitrary threshold level. An arbitrary threshold level is selected for determining the "Peak Count". For this example, the threshold was set at about 40% of the maximum peak value. The Peak Count is a count of the number of pixels for a surface reflection which exceed the threshold level. It should be appreciated that the numbers for the Average Weighting, the Total Weighting and the Peak Count are exemplary and that the values will vary with the scaling used by the particular CCD array, related electronic circuitry and selected threshold level. However, although the magnitudes may be different, the data will still indicate the presence and location of surface coatings.

TABLE 1

| Surface # | Average Weighting | Total Weighting | Peak Count |
| --- | --- | --- | --- |
| 1 | 92 | 47856 | 33 |
| 2 | 54 | 17664 | 26 |

Figure 3:
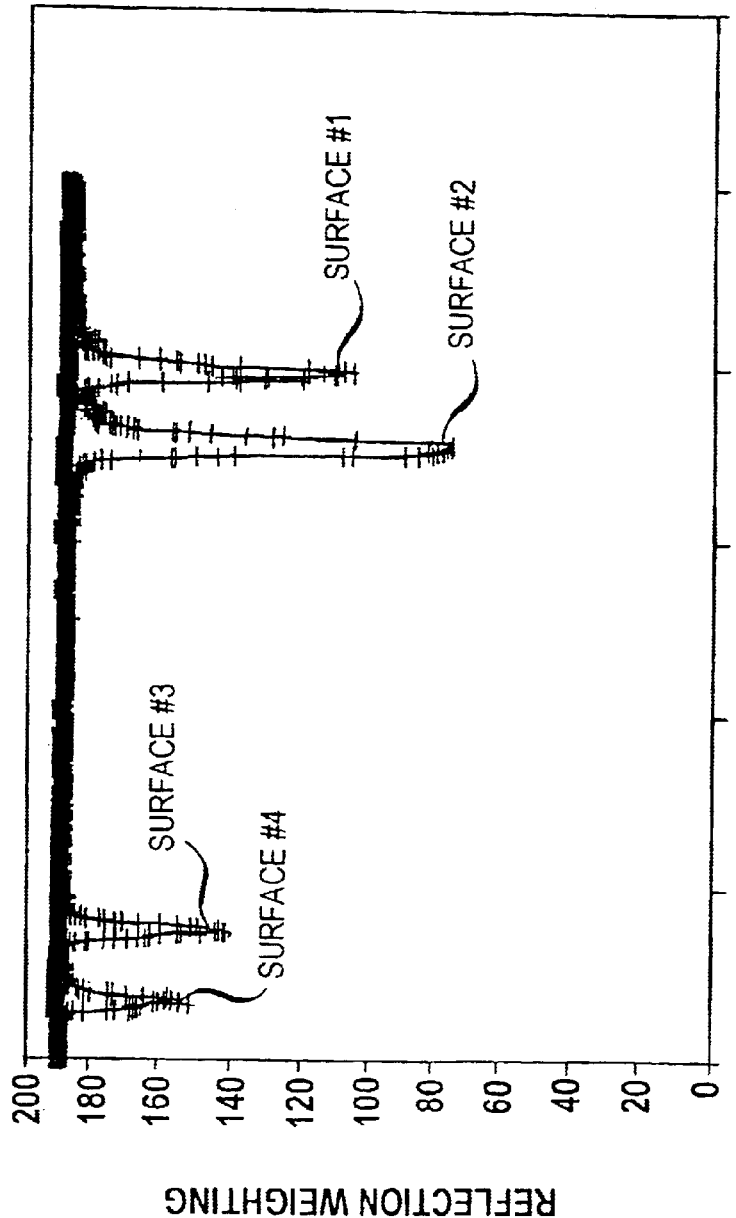
FIG. 3 is a graph showing exemplary reflections from two spaced panes of glass with a transparent reflective coating located on the second surface of the first pane.

FIG. 3 is a graph similar to FIG. 2, except that it shows the sensor readings for a composite formed from two spaced panes of Cardinal Softcoat (Cardsoft) glass separated by a gas and having a Low-E coating on surface #2. Table 2 shows the average and total weightings and peak count for this sample. It should be noted that the highest average weighting, the highest total weighting and the highest peak count are for surface #2.

TABLE 2

| Surface # | Average Weighting | Total Weighting | Peak Count |
| --- | --- | --- | --- |
| 1 | 50 | 17227 | 28 |
| 2 | 81 | 45114 | 34 |
| 3 | 33 | 4461 | 17 |
| 4 | 27 | 840 | 9 |

Figure 4:
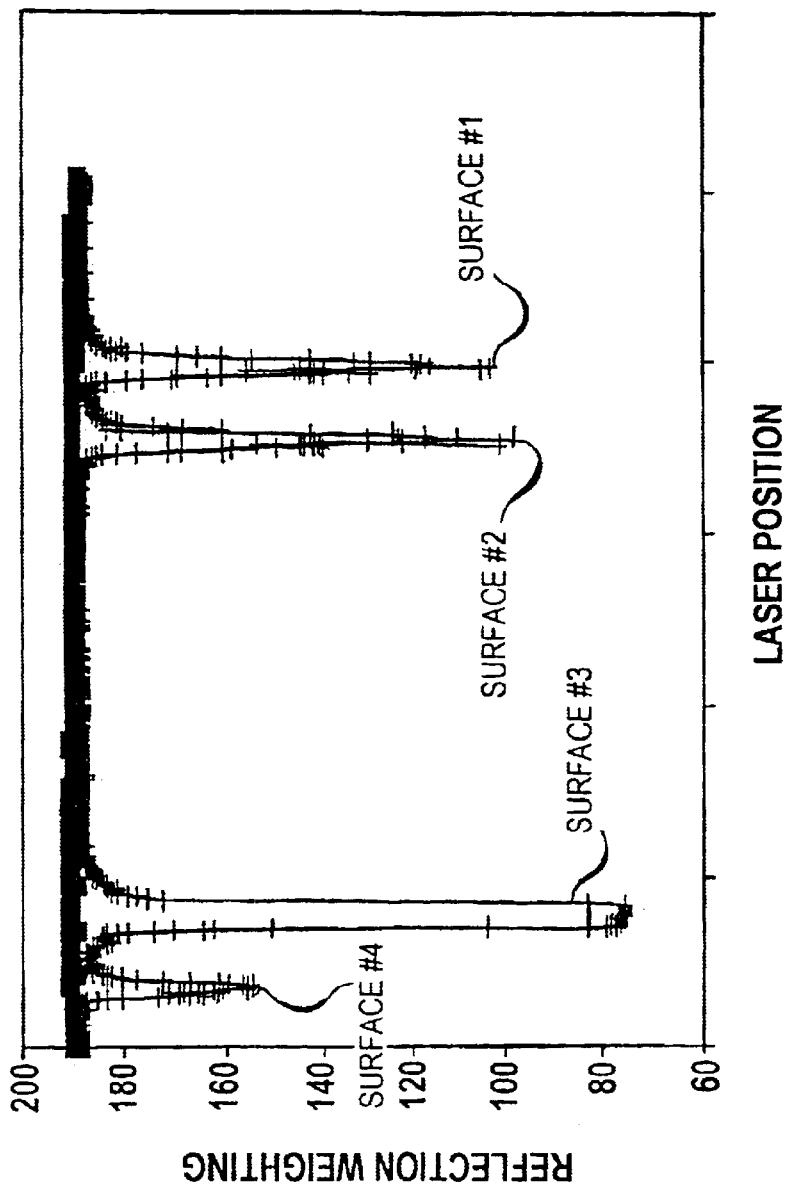
FIG. 4 is a graph showing exemplary reflections from two spaced panes of glass with a transparent reflective coating located on the third surface of the composite or the first surface of the second pane.
Figure 5:
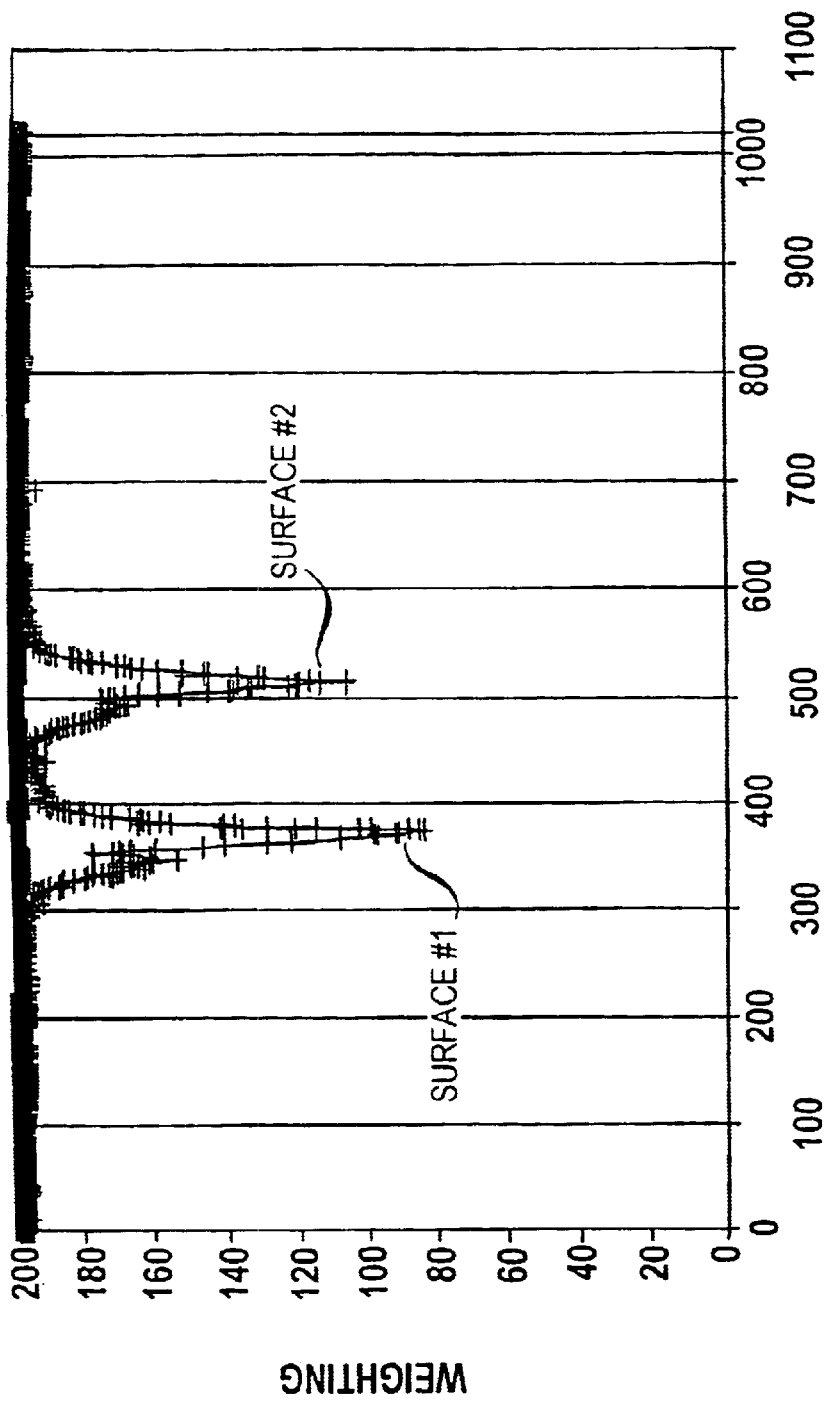
FIG. 5 is a graph showing exemplary reflections from a 0.25 inch sheet of clear float glass having a tin coated side down.
Figure 6:
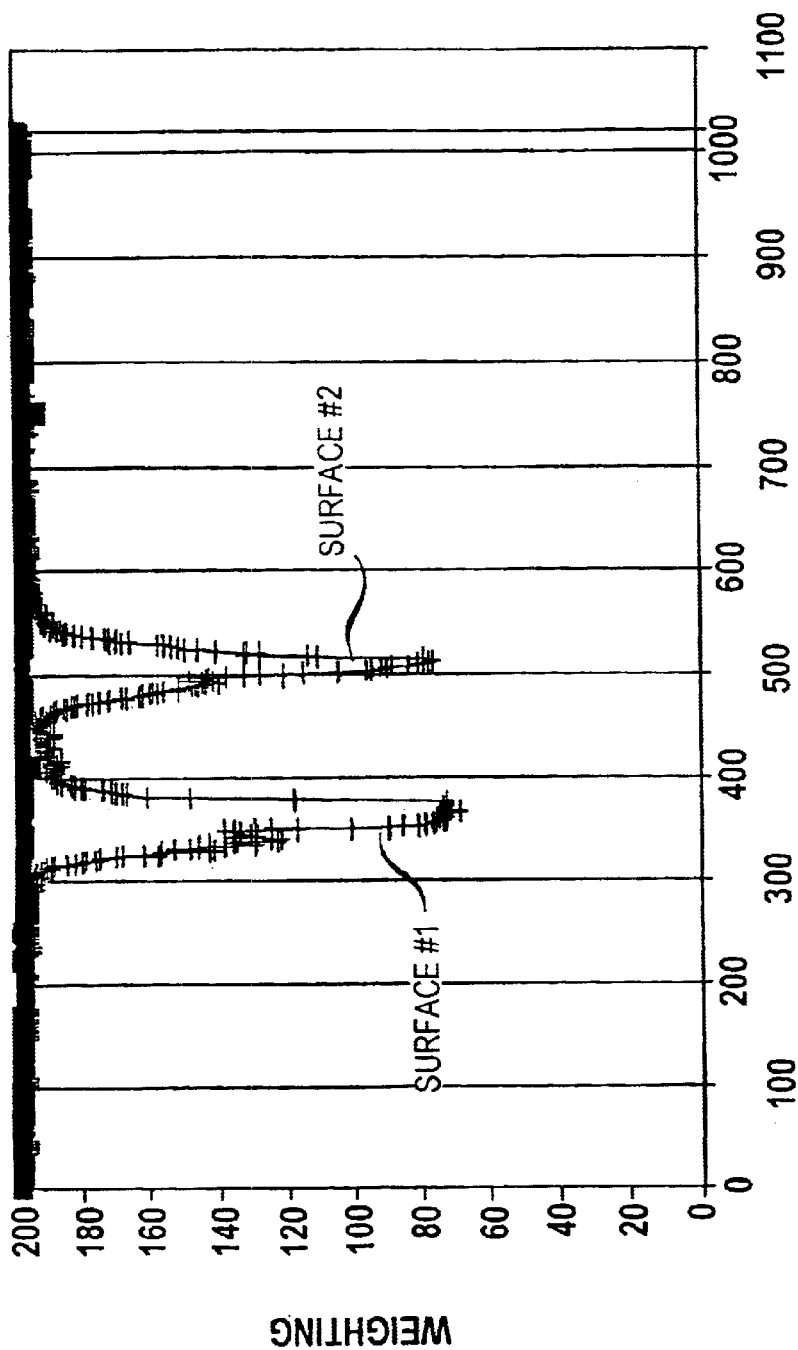
FIG. 6 is a graph showing exemplary reflections from a 0.25 inch sheet of clear float glass having a tin coated side up.
Figure 7:
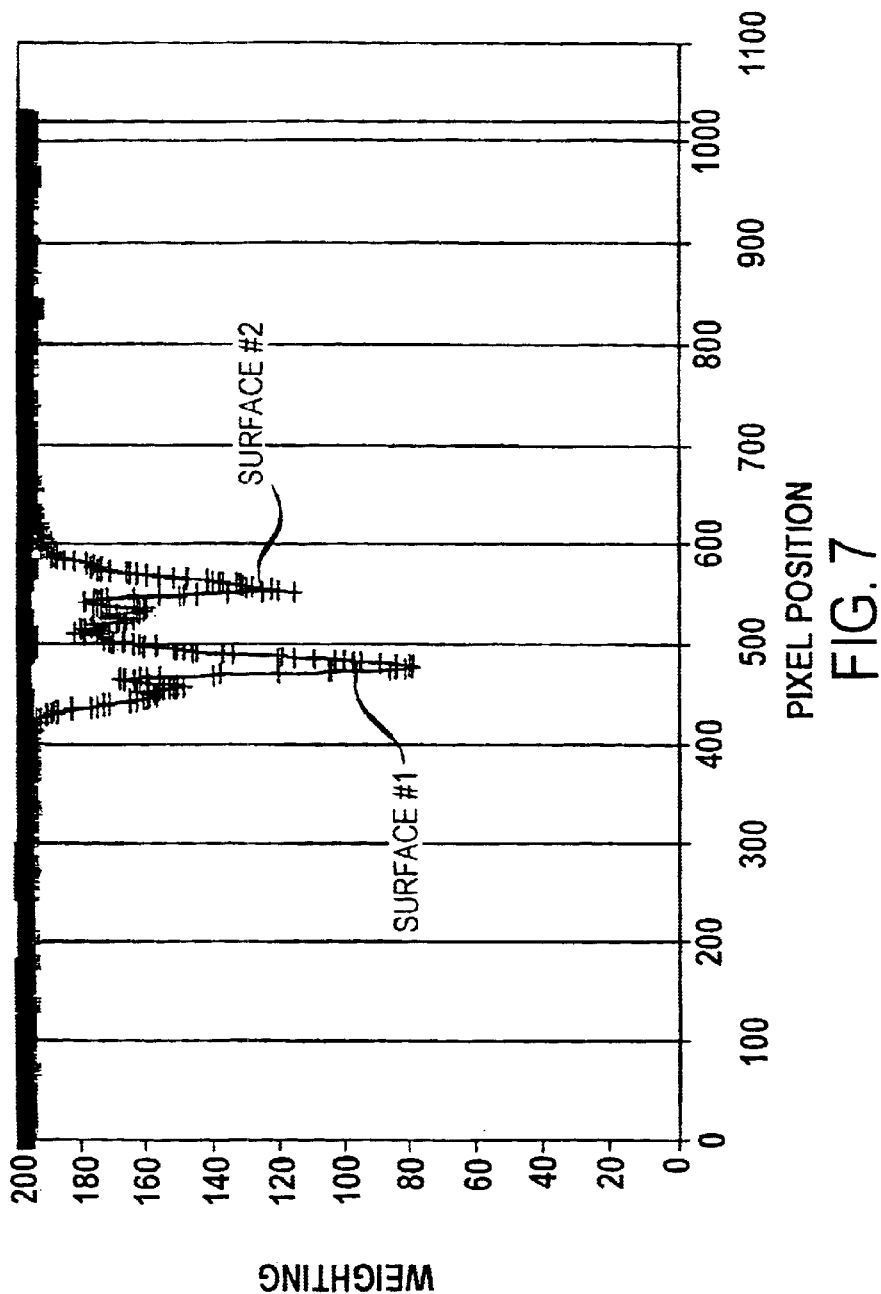
FIG. 7 is a graph showing exemplary reflections from a 0.125 inch sheet of clear float glass having a tin coated side down.

FIG. 4 is a graph showing the sensor readings for a composite formed from the same glass as used in producing the graph of FIG. 3, except that the Low-E coating is located on surface #3 of the composite. Table 3 shows the average and total weightings and peak count for this sample. The highest average weighting, the highest total weighting and the highest peak count are for surface #3.

TABLE 3

| Surface # | Average Weighting | Total Weighting | Peak Count |
| --- | --- | --- | --- |
| 1 | 51 | 15049 | 25 |
| 2 | 53 | 13078 | 22 |
| 3 | 102 | 59220 | 34 |
| 4 | 28 | 2062 | 13 |

Figure 8:
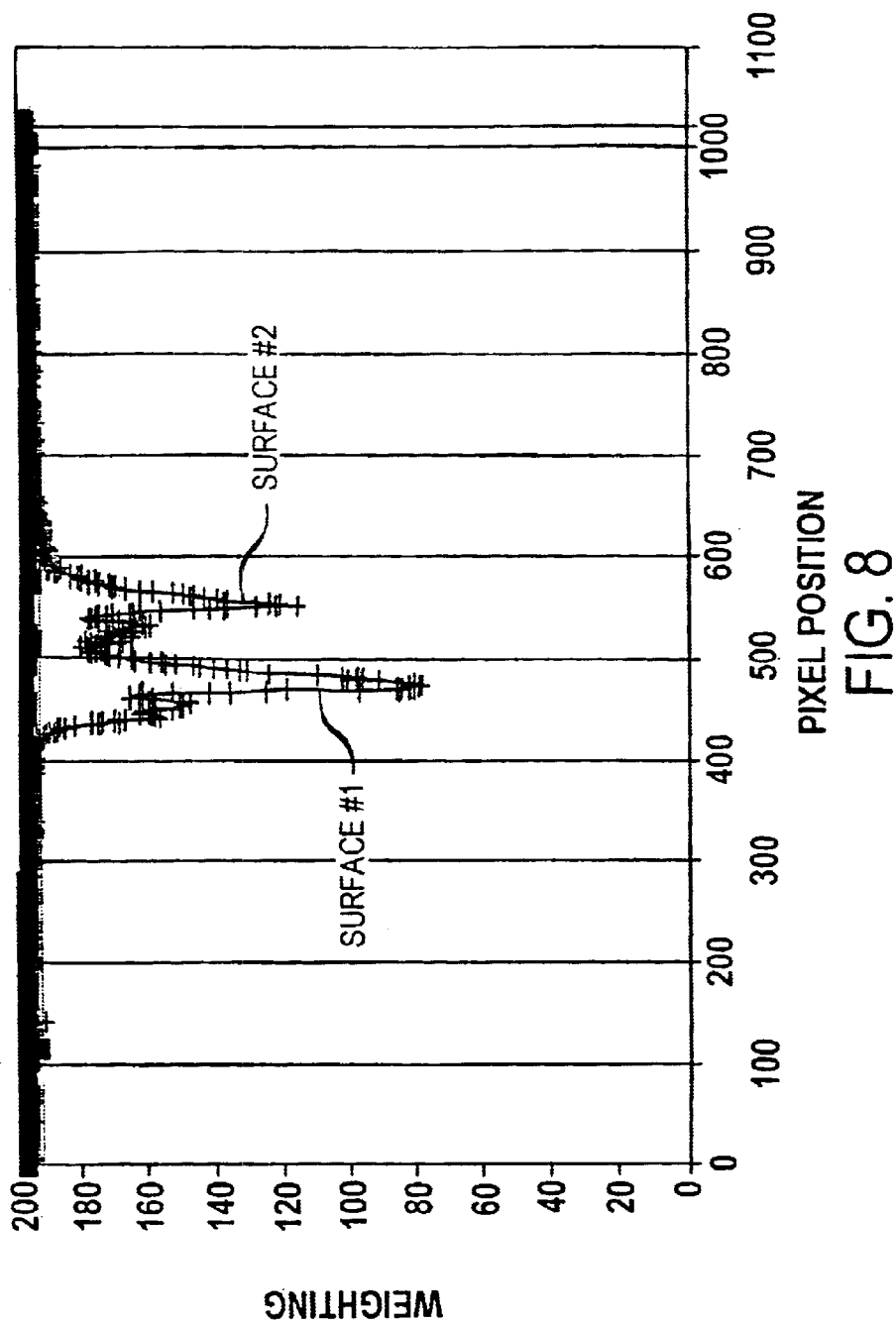
FIG. 8 is a graph showing exemplary reflections from a 0.125 inch sheet of clear float glass having a tin coated side up.

FIGS. 5–8 show the results of traces of metallic oxide on a clear piece of float glass. An algorithm that incorporates location, peak values, intensity and weightings for each sensing element that is affected by the beam, determines the presence and location of the (spectral reflective) metallic oxide traces (tin side). The microprocessor 17 may be programmed to determine a surface weighting ratio by dividing the surface #1 weighting by the surface #2 weighting. For example, using one weighting arrangement, a weighting ratio of 1.48 will indicate the metallic oxide is present on surface #2 (FIG. 5) of a one-quarter inch thick sheet of glass. Meanwhile a ratio of 2.25 will indicate that metallic oxide traces are present on surface #1 (FIG. 6) of the same sheet of glass. As illustrated, the actual ratio will vary with the glass thickness. For a one-eighth inch sheet of the same type of glass, the surface weighting ratio is 6.21 when the coating is on surface #2 (FIG. 7) and the weighting ratio is 8.15 when the coating is on surface #1 (FIG. 8). The example ratios of the weightings from each surface are shown in Table 4. The weightings are dependent upon factors including the strengths of the reflected signals, the frequency of the light source being used and the gain of the sensor circuit. The electronics can be trained for the weighting ratios that are appropriate for the medium under test.

TABLE 4

| Glass Thickness | Tin Side Location | Surface #1 Weighting | Surface #2 Weighting | Weighting Ratio |
|---|---|---|---|---|
| 0.250 inch | Surface #2 | 20043 | 13534 | 1.48 |
| 0.250 inch | Surface #1 | 147226 | 65560 | 2.25 |
| 0.125 inch | Surface #2 | 64317 | 10335 | 6.22 |
| 0.125 inch | Surface #1 | 63850 | 7831 | 8.15 |

Figure 9:
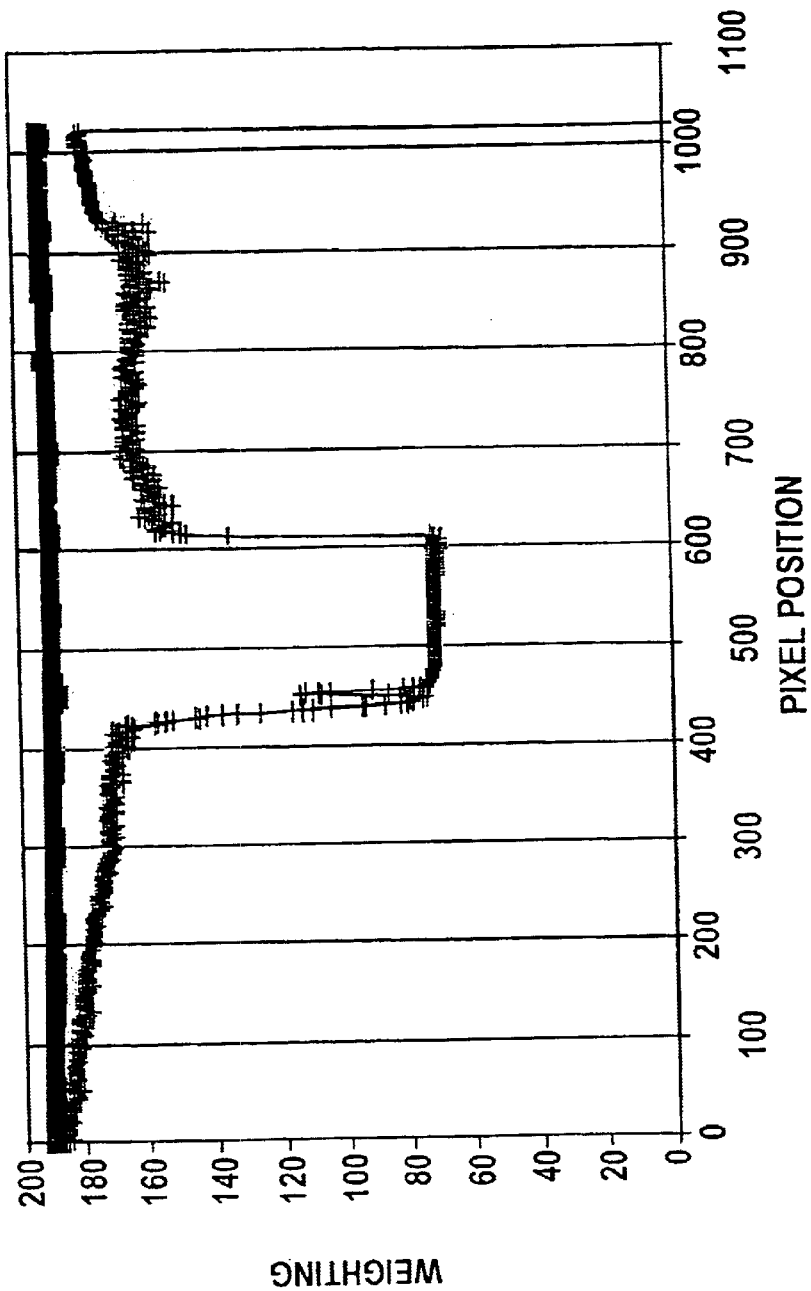
FIG. 9 is a graph showing the total reflected from a single sheet of float glass without surface coatings.
Figure 10:
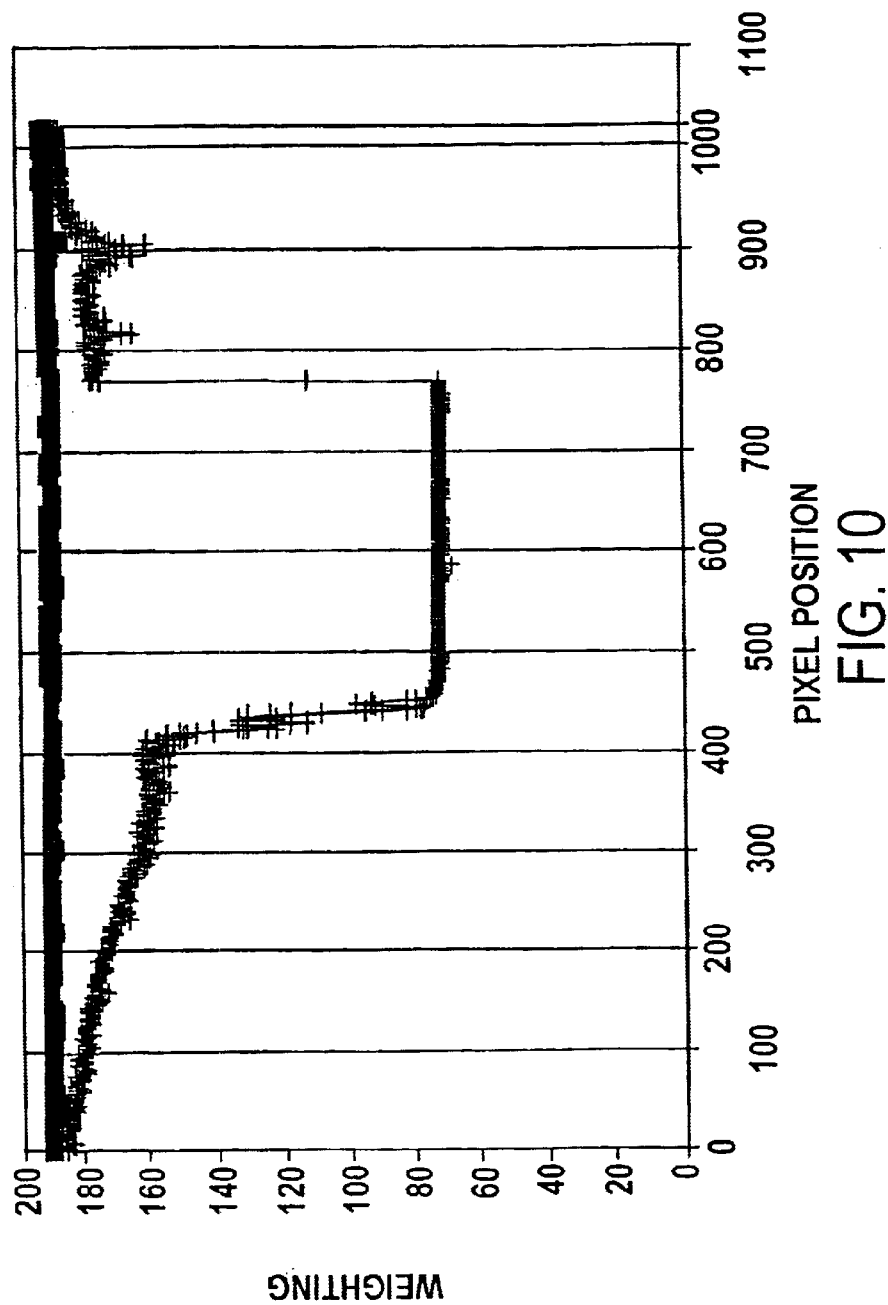
FIG. 10 is a graph showing the total reflected from a sheet of float glass having a Cardinal 178 Low-E surface coating on the second surface.
Figure 11:
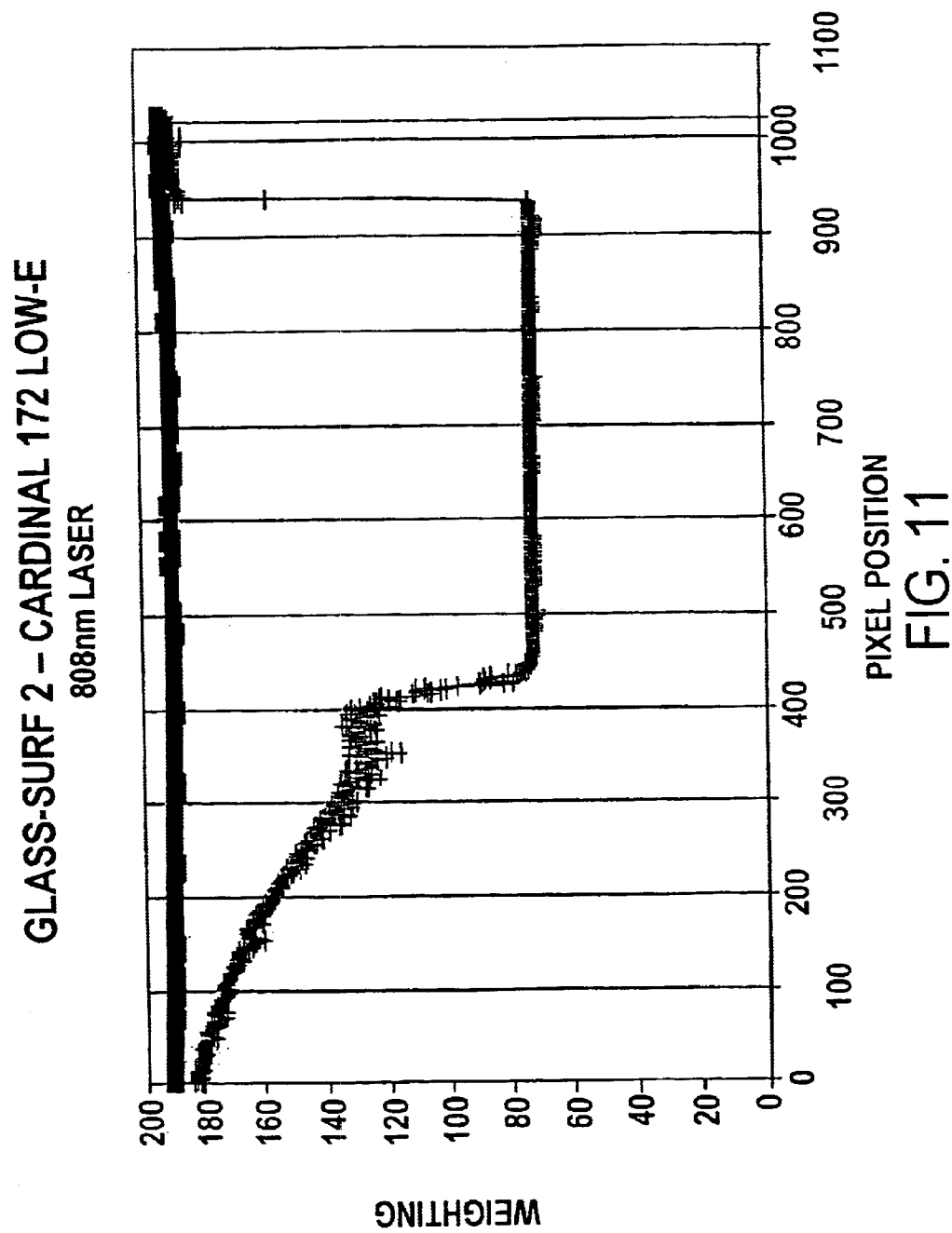
FIG. 11 is a graph showing the total reflected from a sheet of float glass having a Cardinal 172 Low-E surface coating on the second surface.

Typical CCD arrays are extremely sensitive to light levels. In creating the graphs of FIGS. 2–8, either the output of the light source 13 is low or filters sufficiently reduce the level of the light impinging on the CCD array sensor 15 to a level that the individual surface reflection peaks may be measured. If a higher light level impinges on the CCD array sensor or if a slower sensor reading time is used, the peaks for glass surface #1 and surface #2 reflections may blend together to form a single peak, as shown in FIGS. 9–11. In this situation, absence or the presence and location of a Low-E coating can be determined from the width of the single peak or from the total weighting or area under the peak. FIG. 9 shows the single peak for the combined reflections from surface #1 and surface #2 of a single sheet of clear glass without a surface coating. FIG. 10 shows a wider single peak for Cardinal 178 glass with a Low-E coating on surface #2. FIG. 11 shows an even wider single peak for Cardinal 172 glass with a Low-E coating on surface #2. In each case the sensor measures the absolute values from each sample to determine the presence and location of the coating. In FIGS. 2–4 the pulse for surface #1 is to the right and in FIGS. 5–8 the pulse for surface #1 is to the left. This difference is merely from a reversal in the manner in which the information was displayed.

From FIGS. 2–11 of the drawings, it should be noted that the reflections from a coated surface can be stronger or weaker causing more or less CCD pixels to pick up the reflected signal based upon the light frequency chosen. It also will be noted that the intensity of each successive reflection will be of lower magnitude when no coating is present. This is due to the fact that only a portion of the light beam impinging on a surface is refracted towards the next surface and due to any dispersion in the transparent material. In determining the total weight of each reflection, the programmed microprocessor 17 can compensate for the normal decrease in strength of each reflection if desired. It also should be noted, that the measurements for FIGS. 2–11 were performed using a single light source with the reflections sensed by a CCD linear light sensing array. In some cases, a single light source may be used to distinguish between a group of known types of reflective coatings. For example, the width of the broad pulses shown in FIGS. 10 and 11 illustrate the differences between reflections for Cardinal 172 and Cardinal 178 surface coatings.

Figure 12:
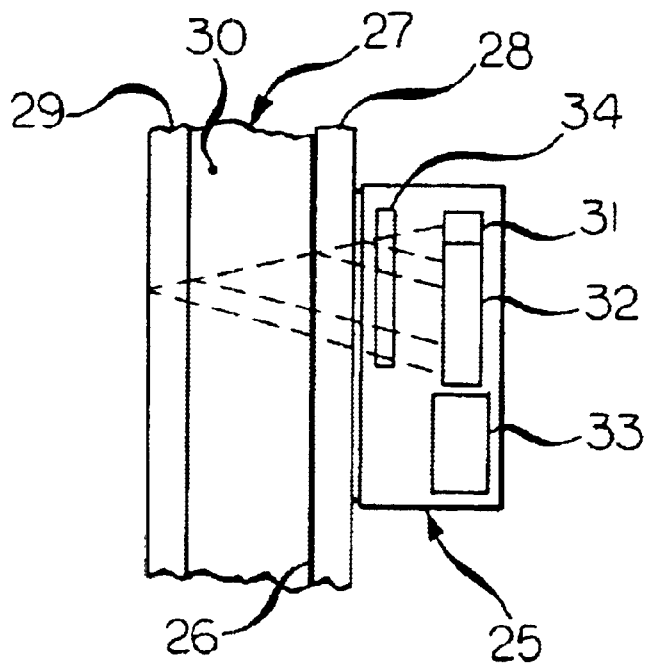
FIG. 12 is a diagrammatic view showing portable apparatus according to a second embodiment of the invention for detecting one or more reflective coatings on one or more surfaces of a single sheet of transparent material or of a composite of spaced sheets of transparent material in the field.

FIG. 12 of the drawings illustrates a portable apparatus 25 according to a further embodiment of the invention for detecting one or more transparent reflective coatings 26 on a surface of a glass composite 27 consisting of first and second sheets 28 and 29 of glass separated by a gas filled space 30. The transparent reflective coating 26 is shown as having been applied to surface #2 of the first glass sheet 28. According to the invention, the apparatus 25 is positioned against surface #1 of the glass sheet 28 for detecting transparent reflective surface coatings. The apparatus 25 may have a single light source 31 and a single light sensor array 32, as described for the non portable apparatus 10 of FIG. 1, which is connected to a programmed microprocessor 33 for determining the presence and location of any surface coatings 26. The apparatus 25 also may determine the thickness of a single sheet of glass or of the thickness of glass panes and of the pane spacing in a glass composite. The pane thickness and spacing may be determined from the spacing of the different surface reflections, as is known in the prior art.

According to an alternate embodiment of the invention, the apparatus 25 is provided with at least two laser or LED light sources having different frequency or wavelength light outputs and with one or more reflected light sensors. Light from the different wavelength light sources will be reflected differently by different surface coatings. In other words, although two different coating materials may reflect the same magnitude or weighting of light at one light wavelength, they will reflect different magnitudes or weightings of light at a different light wavelength. The light sources or transmitters and the light sensor(s) are arranged so that light from each source which is reflected by the surface coating 26 impinges on a sensor and can be independently measured. If a single light sensor is provided for two or more different wavelength light sources, the light sources can be alternately pulsed on so that the light sensor detects the energy level in reflected light from only one frequency light source at a time. Preferably, the light beams reflected from the glass surfaces are passed through a filter 34 to remove unwanted light frequencies, such as from ambient light. Also, either the magnitude of the light from the source or the filter 34 may be used to control the maximum reflected light level at the light sensor(s) to a level suitable for the sensor (s).

Each light beam has a fixed wavelength or a narrow band of wavelengths and is generated by a light source, such as a laser light source or an LED. The reflections from the glass surfaces are detected by a sensor, such as one or more CCD arrays or a row of closely spaced photosensors. The sensor may be, for example, of a type which produce an analog signal having a magnitude which is a function of the magnitude of or energy in the reflected light received by the sensor. Or, the sensors may be of a type which produce an output having a frequency which is a function of the magnitude of energy in the reflected light beam.

It should be appreciated that there are alternate ways for measuring the reflected energy level at different wavelengths. A single light source 31 may be capable of being operated to produce different wavelength light beams. For example, LED's are available which can be operated to produce light having either of two different colors. By switching the light source between different wavelengths, the sensor 32 can measure the energy level in the surface reflections at the different wavelengths. Alternately, the light source 31 may produce a broad spectrum of wavelengths. Different filters 34 may be used for selectively passing to the sensor 32 reflections of different wavelengths or of different bands of wavelengths in the surface reflections.

Figure 13:
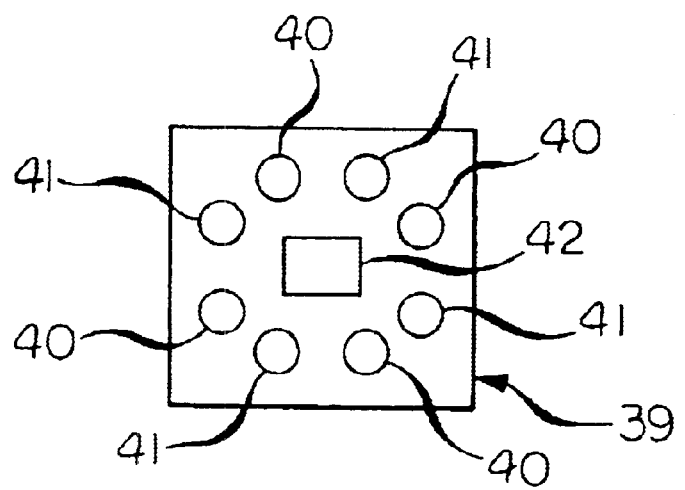
FIG. 13 is a diagram showing a sensor including a ring of alternating frequency light transmitters surrounding a central light receiver according to a further embodiment of the invention.

FIG. 13 shows the light beam producing and sensing arrangement for apparatus 39 for determining the type of coating on a glass surface according to a further embodiment of the invention. The apparatus 39 includes a plurality of light sources 40 having a light output wavelength of 650 nm and a plurality of light sources 41 have a light output wavelength of 850 nm. It should be appreciated that the two wavelengths 650 nm and 850 nm are exemplary and that other wavelength light sources may be used, and that light sources providing more than two wavelengths also may be used. Four light sources 40 and four light sources 41 are shown in an alternating circular fashion surrounding a single light sensor 42. Preferably, each light source 40 and 41 each provide a conical light beam so that surface reflections will impinge on the sensor 42. Conical light beams may be produced, for example, by LED's or by an unfocused or dispersed laser beam. An advantage of the LED's is they do not require any eye safety considerations for a portable apparatus 39. By surrounding the sensor 42 with the light sources 40 and 41, the sensor 42 will detect surface reflections even when the apparatus 39 is not accurately aligned with the glass surfaces or when the glass surfaces are not precisely parallel. In the arrangement illustrated in FIG. 13, the light sources 40 and the light sources 41 are alternately pulsed so the sensor 42 will produce separate data for each wavelength. By surrounding the sensor 42 with the light sources 40 and 41, light from one or more light source will be reflected to the sensor 42, even when the reflecting surface coating is not precisely parallel to the apparatus 39.

Figure 14:
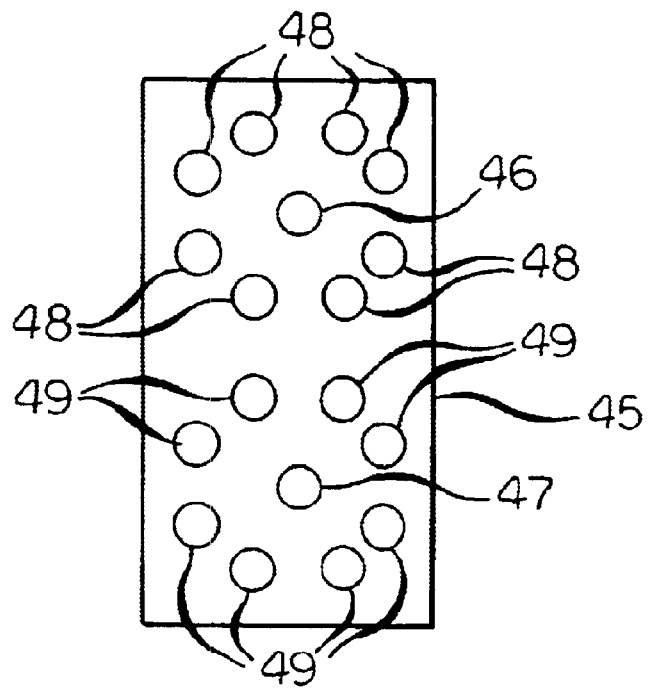
FIG. 14 is a diagram showing a modified sensor arrangement with two spaced light transmitters of different frequencies, each surrounded by a ring of reflected light receivers according to a further embodiment of the invention.

FIG. 14 shows modified sensor apparatus 45. A 650 nm light source 46 and a 850 nm light source 47 are spaced apart. A plurality of sensors 48 surround the source 46 and a different plurality of sensors 49 surround the source 47. In this arrangement, the sensors 48 which surround the light source 46 only receive reflections of light from the source 46. Similarly, the sensors 49 which surround the light source 47 only receive reflections of light from the source 47. Consequently, both light sources 46 and 47 may operate at the same time. Normally, the light sources 46 and 47 will direct expanding conical light beams about an axis which is perpendicular to the surfaces under test. By surrounding the light sources 46 and 47 with sensors 48 and 49, one or more sensors will receive reflected light from each source, even when the reflecting surface coating is not precisely parallel to the apparatus 45.

Figure 15:
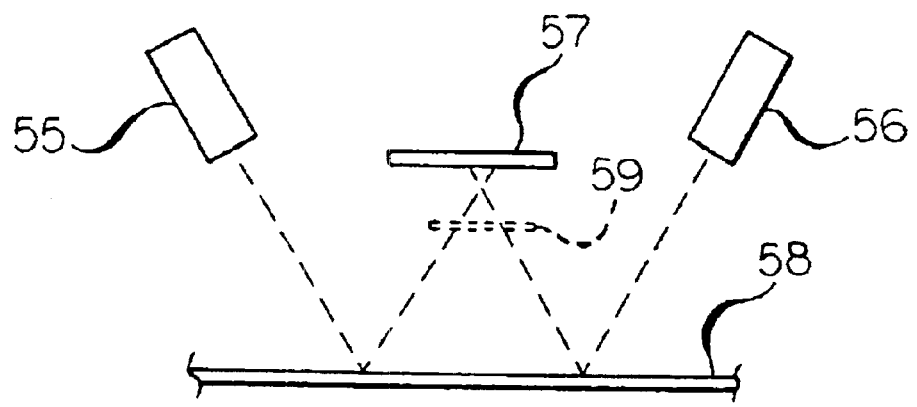
FIG. 15 is a diagram showing a sensor arrangement according to a further embodiment of the invention.

FIG. 15 shows a further sensor arrangement wherein two laser light beam sources 55 and 56 are positioned on opposite sides of a CCD array sensor 57. The lasers 55 and 56 are angled relative to the CCD array sensor 57 such that reflections of both light beams from surfaces of a sheet of glass 58 or other transparent medium under test impinge on the CCD array 57. The lasers 55 and 56 produce different wavelength light beams. Since a single CCD array sensor 57 is used with the two laser light sources 55 and 56, the laser light sources 55 and 56 are alternately turned on so that the CCD array sensor 57 will produce separate reflection magnitude data for each light wavelength. As previously described, a suitable light filter 59 may be provided so that the sensor 57 sees primarily light having wavelengths in the range of that produced by the lasers 55 and 56.

When multiple light sensors are provided, the outputs from the sensors are combined to produce reflected energy data for each wavelength. The total reflected energy for one wavelength may be used to determine if one or more of the reflected amplitude signals indicates the presence, location, and/or type of a coating. The apparatus includes a microprocessor which can be programmed to store the data in a table. Table 5 illustrates exemplary magnitudes or weightings for the coated surface which were obtained from different samples of glass when using light transmitters having a wavelength of about 875 nm. The values may be taught to the microcomputer by testing samples of the different coatings and of different surface coating locations for various samples of glass or other transparent material and for various commercial composites. The presence, location and/or type of a coating is determined by comparing the surface reflection energy levels with the stored information for the different samples. This device may include an array of LED indicators which are selectively illuminated to indicate the presence of a reflective surface coating and the surface location of the reflective coating. Alternately, other types of indicators may be provided. For example, a reflected energy magnitude signal may be provided for manually comparing with a table of different reflected energy magnitudes for coatings on the different surfaces of standard glass. By comparing the indicated magnitude with the readings for the particular type of glass being measured, the presence and surface location of any coating will be readily apparent. These indicators also may provide information on the thickness of the material and the spacing of sheets forming a composite.

TABLE 5

| Glass Manufacturer | Surface Location Of Coating | | |
|---|---|---|---|
| And Type | #1 | #2 | #3 |
| Clear Float Glass (no coating)* | 39 | | |
| PPG 100* | 88 | | |
| PPG 100* | | | 68 |
| PPG 1000* | 176 | | |
| PPG 1000* | | 125 | |
| Cardinal 172** | | 122 | |
| Cardinal 172** | | | 70 |
| Cardinal 178** | | 70 | |
| Cardinal 178** | | | 53 |

*Single pane glass
**Double pane glass

The readings in Table 5 are taken from different sides of the glass, where surface #1 is the surface closest to the measuring apparatus. It should be noted that it is possible for readings to be taken from surface 4 of a double pane composite. It also should be noted that the readings are all relative and depend on variables such as the intensity or energy of the light source, frequency of the light source and the gain of the circuitry.

When multiple light sensors are provided, the outputs from the sensors are combined to produce data which is proportional to the magnitude of the reflected light at each wavelength. When a different group of sensors are provided for each light wavelength, the outputs from sensors for each wavelength are independently combined. The apparatus includes a programmed microcontroller, microprocessor or computer, which uses this data for obtaining a curve that is indicative of the type of coating on the surface of the glass. FIG. 16 illustrates the types of curves, which may be obtained when using light transmitters having wavelengths of about 635 nm and about 875 nm. These curves may be taught to the microcontroller, microprocessor or computer by testing samples of different coatings. A particular coating type or manufacturer is identified by comparing the results from an unknown sample with the previously taught curves. By taking reflection readings at two different wavelengths, different coating types can be discriminated between, even though they may have the same reflective reading at one of the two wavelengths. This is illustrated, for example, between the lines 65 and 66, which have the same value at the lower wavelength, but totally different slopes and different values at the higher wavelength. Although only two wavelength light beams are described in the illustrated embodiment of the invention, it will be appreciated that more than two different wavelength light sources may be provided so that additional points may be plotted for the curves shown in FIG. 16. FIG. 16 clearly points out that two or more light sources can be used to determine the type of coating that is present. This is due to the fact that the magnitude of the reflected light signal for each coating will depend upon the frequency of the light source used.

The above apparatus can determine the type of transparent reflective coating left on the glass or other transparent medium from the manufacturing process or placed upon the medium to enhance its capability. For example, reflected energy magnitude data may be provided to a microcontroller, microprocessor or computer for comparing with a table of data on different reflected energy magnitudes for coatings on the different surfaces of standard glass. By comparing the indicated magnitude with the readings for the particular glass being measured, both the presence and surface location of any coating and the type of coating can be determined.

It will be appreciated that various modifications and changes may be made to the above described preferred embodiments of the invention without departing from the scope of the following claims. As indicated above, the invention may be used for detecting surface coatings both on glass and on other transparent materials. Although the preferred light sources are either lasers or LED's, it will be appreciated that other types of light sources may be used. In order to determine the type of surface coating, the light beams for the two readings must each have a single wavelength or must fall within a narrow range of wavelengths. Although the preferred light sensor is a CCD array, it also should be appreciated that other known types of light sensors may be used in measuring the magnitude of the light beam reflections.

What is claimed is:

1. A method for detecting any transparent light reflective surface coating on any surface of a sheet of transparent material having at least two generally parallel surfaces comprising the steps of:
   a) from one side of said sheet of transparent material, directing a light beam at an angle to the surfaces of said sheet of transparent material whereby such light beam is reflected by surfaces of said sheet of transparent material;
   b) sensing the energy level in light beam reflections from at least two surfaces of said sheet of transparent material; and
   c) determining from the sensed energy level of the light beam reflections the presence of any light reflective surface coatings on said sheet of transparent material.

2. A method for detecting any transparent light reflective surface coating on a sheet of transparent material, as set forth in claim 1, and wherein said step of determining from the energy level of light beam reflections the presence of any reflective surface coatings further determines the surface location on said sheet of transparent material of any light reflective surface coatings.

3. A method for detecting any transparent light reflective surface coating on a sheet of transparent material, as set forth in claim 1, wherein the sheet of transparent material comprises a composite formed from at least two substantially parallel spaced sheets of transparent material, and wherein said step of determining from the energy level of light beam reflections the presence of any reflective surface coatings further determines the surface location on said composite of any light reflective surface coatings.

4. A method for detecting any transparent light reflective surface coating on a sheet of transparent material, as set forth in claim 1, and wherein the presence of any light reflective surface coatings on said sheet of transparent material are determined by comparing the energy levels of the light beam reflections from each surface.

5. A method for detecting any transparent light reflective surface coating on a sheet of transparent material, as set forth in claim 4, and wherein the energy levels of the light beam reflections from each surface are compared with each other.

6. A method for detecting any transparent light reflective surface coating on a sheet of transparent material having at least two generally parallel surfaces comprising the steps of:
   a) directing a light beam at an angle to the surfaces of said sheet of transparent material whereby such light beam is reflected by surfaces of said sheet of transparent material;
   b) sensing the energy level in light beam reflections from surfaces of said sheet of transparent material; and
   c) determining from the sensed energy level of the light beam reflections the presence of any light reflective surface coatings on said sheet of transparent material; and
   wherein the energy levels of the light beam reflections from each surface are compared with stored data corresponding to the energy levels of light beam reflections from the surfaces of known surface coated and uncoated samples of transparent material.

7. A method for detecting any transparent light reflective surface coating on a sheet of transparent material, as set forth in claim 1, and further including the step of generating said light beam from at least one source selected from the group consisting of a laser and an LED.

8. A method for detecting any transparent light reflective surface coating on a sheet of transparent material having at least two generally parallel surfaces comprising the steps of:
   a) directing a light beam at an angle to the surfaces of said sheet of transparent material whereby such light beam is reflected by surfaces of said sheet of transparent material;
   b) sensing the energy level in light beam reflections from surfaces of said sheet of transparent material; and
   c) determining from the sensed energy level of the light beam reflections the presence of any light reflective surface coatings on said sheet of transparent material; wherein at least two light beams are generated from at least two different light sources selected from the group consisting of a laser and an LED and having different wavelengths, wherein light beams from said at least two different sources are directed at an angle to surfaces of said sheet of transparent material whereby such light beams are reflected by surfaces of said sheet of transparent material, wherein the energy levels in light beam reflections from surfaces of said sheet of transparent material are sensed for at least two different wavelengths, and wherein the presence and type of any light reflective surface coatings on said sheet of transparent material are determined from the energy levels of the light beam reflections at least two wavelengths.

9. A method for detecting any transparent light reflective surface coating on a sheet of transparent material, as set forth in claim 8, and wherein the energy levels in light beam reflections from surfaces of said sheet of transparent material are sensed for at least two different wavelengths by alternately operating at least one light source for each wavelength, and directing different wavelength light beam reflections from surfaces of said sheet of transparent material at a sensor.

10. A method for detecting any transparent light reflective surface coating on a sheet of transparent material, as set forth in claim 8, and wherein the energy levels in light beam reflections from surfaces of said sheet of transparent material are sensed for at least two different wavelengths by directing different wavelength light beam reflections from surfaces of said sheet of transparent material at different sensors.

11. A method for detecting any transparent light reflective surface coating on a sheet of transparent material having at least two generally parallel surfaces comprising the steps of:

a) directing a light beam at an angle to the surfaces of said sheet of transparent material whereby such light beam is reflected by surfaces of said sheet of transparent material;

b) sensing the energy level in light beam reflections from surfaces of said sheet of transparent material; and c) determining from the sensed energy level of the light beam reflections the presence of any light reflective surface coatings on said sheet of transparent material; and wherein a light beam having light energy in at least two different wavelengths is directed at an angle to the surfaces of said sheet of transparent material whereby light energy at each of said at least two different wavelengths is reflected by any reflective surface coating on a surface of said sheet of transparent material, wherein the energy levels in light beam reflections from surfaces of said sheet of transparent material are sensed for at least two different wavelengths, and wherein the presence and type of any light reflective surface coatings on said sheet of transparent material are determined from the energy levels of the light beam reflections at said at least two different wavelengths.

12. A method for detecting any transparent light reflective surface coating on a sheet of transparent material, as set forth in claim 11, and wherein the energy levels in light beam reflections from surfaces of said sheet of transparent material are sensed for at least two different wavelengths by filtering such reflections to independently pass light beam reflections at substantially each of said at least two different wavelengths.

13. A method for detecting any transparent light reflective surface coating on a sheet of transparent material, as set forth in claim 12, and wherein said light beam reflections are alternately filtered to pass substantially each of said two different wavelengths to a sensor.

14. A method for detecting any transparent light reflective surface coating on a sheet of transparent material having at least two generally parallel surfaces comprising the steps of:

a) directing a light beam at an angle to the surfaces of said sheet of transparent material whereby such light beam is reflected by surfaces of said sheet of transparent material;

b) sensing the energy level in light beam reflections from surfaces of said sheet of transparent material; and c) determining from the sensed energy level of the light beam reflections the presence of any light reflective surface coatings on said sheet of transparent material and the type of any such coatings.

15. Apparatus for detecting transparent light reflective surface coatings on any surface of a sheet of transparent material having at least two generally parallel surfaces, said apparatus comprising at least one light source adapted to be mounted to one side of a sheet of material for directing at least one light beam at an angle to surfaces of such sheet of material whereby a portion of such at least one light beam is reflected by each surface of such sheet of material, at least one light sensor arranged for independently sensing the energy level of each light beam reflection from surfaces of such sheet of material, and a processor programmed for determining the presence of any reflective surface coatings on surfaces of such sheet of material from the sensed energy level of light beam reflections from surfaces of such sheet of material.

16. Apparatus for detecting a transparent light reflective surface coating on a sheet of transparent material, as set forth in claim 15, and wherein said at least one light source is selected from the group consisting of a laser and an LED.

17. Apparatus for detecting a transparent light reflective surface coating on a sheet of transparent material, as set forth in claim 15, and wherein said at least one sensor is selected from the group consisting of an CCD array and a photosensor.

18. Apparatus for detecting a transparent light reflective surface coating on a sheet of transparent material having at least two generally parallel surfaces, said apparatus comprising at least one light source mounted for directing a light beam at an angle to surfaces of a sheet of material whereby a portion of such light beam is reflected by each surface of such sheet of material, at least one light sensor arranged for independently sensing the energy level of each light beam reflections from surfaces of such sheet of material, and a processor programmed for determining the presence of any reflective surface coatings on surfaces of such sheet of material from the sensed energy level of light beam reflections from surfaces of such sheet of material, and wherein said at least one light source comprises at least one first light source adapted to generate light beams having a first wavelength and at least one second light source adapted to generate light beams having a second wavelength different from said first wavelength.

19. Apparatus for detecting a transparent light reflective surface coating on a sheet of transparent material, as set forth in claim 18, and wherein said light sources are mounted to direct light beam reflections from surfaces of such sheet of material at the same sensor.

20. Apparatus for detecting a transparent light reflective surface coating on a sheet of transparent material, as set forth in claim 19, including a plurality of said first light sources and a plurality of said second light sources, and wherein said first and second light sources are alternately mounted in a circle around said light sensor, and wherein said programmed processor is programmed to alternately activate said first light sources and said second light sources whereby said sensor alternately measures the energy in surface reflections for each light wavelength.

21. Apparatus for detecting a transparent light reflective surface coating on a sheet of transparent material, as set forth in claim 18, and wherein said at least one light source includes at least one first light source and at least one second light source, wherein said at least one light sensor includes at least one first sensor and at least one second sensor, wherein said at least one first light source is mounted to direct light beam reflections from surfaces of such sheet of material to said at least one first sensor, and wherein said at least one second light source is mounted to direct light beam reflections from surfaces of such sheet of material to said at least one second sensor.

22. Apparatus for detecting a transparent light reflective surface coating on a sheet of transparent material, as set forth in claim 21, wherein said at least one first source and said at least one second light source are spaced apart, wherein said at least one first sensor comprises a plurality of first sensors mounted in a circle about said first light source for sensing light beam reflections from surfaces of such sheet of material from said first light source, and wherein said at least one second sensor comprises a plurality of second sensors mounted in a circle about said second light source for sensing light beam reflections from surfaces of such sheet of material from said second light source.

23. Apparatus for detecting a transparent light reflective surface coating on a sheet of transparent material, as set forth in claim 15, wherein said light beam reflections have a wavelength including at least a predetermined wavelength, and further including a light filter adapted to reduce ambient light having wavelengths other than substantially said predetermined wavelength from reaching said at least one light sensor.

* * * * *